US00PP13460P2

(12) United States Plant Patent
Vardi et al.

(10) Patent No.: US PP13,460 P2
(45) Date of Patent: Jan. 7, 2003

(54) CITRUS TREE NAMED 'MORIA'

(75) Inventors: Aliza Vardi, Ramat Gan (IL); Pinchas Spiegel-Roy, Ramat-Gan (IL); Ahuva Frydman-Shani, Ramat-Gan (IL); Avraham Elchanati, Holon (IL); Hana Neumann, Hemed (IL)

(73) Assignee: State of Israel - Ministry of Agriculture and Rural Development, Tel Aviv (IL)

( * ) Notice: Subject to any disclaimer, the term of this patent is extended or adjusted under 35 U.S.C. 154(b) by 0 days.

(21) Appl. No.: 09/716,477

(22) Filed: Nov. 20, 2000

(51) Int. Cl.[7] ..... A01H 5/00
(52) U.S. Cl. ..... Plt./202
(58) Field of Search ..... Plt./202

*Primary Examiner*—Kent L. Bell
(74) *Attorney, Agent, or Firm*—Barbara S. Kitchell

(57) ABSTRACT

A new variety of mandarin citrus tree is described that is distinguished by a long ripening period, fruit having a low seed number (0–6 seeds per fruit) and flowers having anthers bearing pollen with low pollen fertility.

2 Drawing Sheets

FIELD OF THE INVENTION

A new mandarin citrus tree of the mandarin tree *Citrus reticulata* is described. The new variety named 'Moria' is desirable to the consumer because of the flavor of the juice and low seed number (0–6 seeds per fruit) and late ripening time (January to mid-April).

BACKGROUND OF THE NEW TREE

The present invention relates to a new distinct variety of mandarin tree *Citrus reticulata* developed by inventors Aliza Vardi, Pinchas Spiegel-Roy, Avraham Elchanati, Ahuva Frydman-Shani, and Hana Neumann in Bet Dagan, Israel from a selection of plants grown from irradiated bud wood of the cultivar 'Murcott'.

Asexual reproduction by conventional bud grafting of the new variety in Israel by grafting has shown that the new characteristics are stabilized and permanently fixed through successive propagations.

The objective in breeding the present new tree variety, known by the cultivar name 'Moria', was to obtain a late ripening mandarin citrus tree bearing fruit with few or no seeds. In the spring of 1986 and 1987 about 400 buds of an easy peeling mandarin cultivar, 'Murcott', were irradiated at the Nahal Soreq Nuclear Center, Yavne, Israel, by exposure to 3.5–4.0 kh of gamma radiation from a Co60 source. Sour orange nucellar rootstocks were bud grafted with the individual buds of irradiated 'Murcott' bud wood and labeled $mV_1$. Six to nine months after grafting the irradiated budwood, individual buds from the $mV_1$ plants were re-grafted on Sour orange nucellar rootstocks to establish about 700 $mV_2$ plants.

Field planting was established from container grown $mV_2$ plants in the spring of 1988 and 1989. The first fruits were observed in January–March 1990 and again in 1991 and 1992.

One of the selections, designated 3/38/55, had medium to large size orange color fruit and was easy to peel. This selection was distinguished from 'Murcott' as having fruit with 0–6 seeds compared with 15–30 seeds for 'Murcott'. The selection typically had 0–6 seeds per fruit.

3/38/55 has flowers with low pollen fertility with 6% of the pollen grains typically stained with acetocarmine compared with 92% for 'Murcott'.

SUMMARY OF THE INVENTION

The new tree, designated 'Moria' was characterized by fruit with very few seeds and flowers having anthers bearing pollen with low fertility. Table 1 compares some of the characteristics of the new cultivar, named 'Moria', and the parent 'Murcott'.

TABLE 1

| Tree | Fruit color | Peelability | Seeds/fruit | Pollen fertility[1] |
|---|---|---|---|---|
| 3/38/55 'Moria' | Orange RHS 28B | Easy | 0–6 | 6% |
| 'Murcott' | Orange RHS 28A | Easy | 15–30 | 92% |

[1]Estimated by Acetocarmine staining

The following is a detailed description of the new mandarin citrus based on observations made under typical Israeli grove conditions.

The tree shape and fruit appearance are similar to that of 'Murcott'. The tree is vigorous. Small thorns, 1 mm to 3 mm are usually present in the leafy part of branches, especially in the lower portion and on the lower part of fruit bearing branches. Main branches have an upright attitude and young shoots have no anthocyanin coloration at the tip.

The bearing of the tree is regular and the productivity is relatively high, about the same as for 'Murcott'. The canopy is moderately dense and there is little tendency to form water sprouts from scions. After pruning, the newly formed branches grow upright. The bark of the young shoots is initially smooth and green gradually turning into a smooth yellow-green. The chromosome number from the morphological characteristics of the tree is assumed to be the same as the parent 2n=18.

The leaves are similar to that of 'Murcott'. They are small to medium in size, lanceolate, and sharp pointed. Leaf blades are firm, without undulation and slightly concave in cross section. Petioles are without wings or have rudimentary wings.

The characteristics of the flowering and the flower part are similar to those of 'Murcott'. Flowering for both occurs at the end of March or the first half of April as measured in Bet Dagan, Israel. Both 'Moria' and 'Murcott' produce about the same number of flowers and flower drop for both occurs in April. Terminal flower buds have no anthocyanin coloration. Flowers are borne singly and have an average number of stamens (about 20) with complete style development. Anther color is pale yellow. Pollen fertility is low as indicated by the observation that only 6% of the pollen grains were stained with acetocarmine in a test conducted at The Agricultural Research Organization, the Volcani Center, as compare with stainability of about 92% for Murcott pollen grain.

The fruit has few seeds, about 0 to 6 seeds, even when optimal pollination conditions are employed. This compares with about 27 seeds per fruit in 'Murcott'. In other respects the fruit characteristics are in the range of the parent cv. 'Murcott'. The fruit shape is oblate and it is medium sized. When 50 fruit were measured, the fruit had an average weight 115 grams, and average height 52 mm, and an average diameter 110 mm. The fruit has a moderately depressed stalk end. The fruit surface is usually smooth with a yellow orange color, 23B on The Royal Horticultural Society of London Colour Chart, and bears an average number of conspicuous rind oil glands. Fruit color and ripening do not differ from outside of the canopy to the inside, but the fruit color of the outside canopy are a little brighter as compare to the fruit color of the inside canopy. There is no persistence of the style and the areola is not completely developed. A navel is absent or very rare. The rind is thin and easy to peel.

The color of the albedo is white and the flesh is orange in color. The fruit contains 9–11 segments and is very juicy. The external color of the seeds is white when fresh. The internal seed coat is greyed orange and the cotyledons are green white. Polyembryony is similar to that of the parent 'Murcott'. The seed sizes, shape and texture are similar to that of the parent 'Murcott'. The fruit reaches maturity late in the season as does 'Murcott', which in Israel was February to April. The ripening of the fruit on the tree and within the fruit is uniform. Fruit remaining on the tree does not regreen and does not begin to lose quality until end of April. If there is a heavy crop and the fruits are not picked before March it may becomes alternate bearing (light crop the following season). Pre-harvest drop of both developed and undeveloped fruit is similar to that of the parent cv 'Murcott'. The juice has an excellent test and flavor.

DESCRIPTION OF THE PHOTOGRAPHS

The new citrus tree is illustrated in the accompanying photographs.

Sheet one depicts a typical view of the new cultivar.

Sheet two depicts a typical fruit of the new cultivar (bottom) showing a single seed compared with several seeds in the parental cultivar 'Murcott' (top). The exterior of the fruit is shown as well as transverse midsections in a plane substantially perpendicular to the axis.

DESCRIPTION OF THE NEW TREE

The following is a detailed description of the new mandarin citrus variety 'Maria' based on observations made under typical Israeli grove conditions. Observations were made on trees approximately 4–5 years old. Colors are based on R.H.S. color designations from The Royal Horticultural Society Colour Chart.

Tree:

*Origin.*—Irradiation of cv. 'Murcott'.

*Classification.*—Botanical: *Citrus reticulata. Common: Mandarin citrus. Cultivar: 'Moria'.*

*Shape.*—Upright, irregular.

*Thorns.*—1–3 mm length (leafy part of branches, mostly on lower part of fruit bearing branches).

*Branching.*—Upright (after pruning), young shoots have no anthocyanin coloration at tip.

*Canopy.*—Moderately dense, little tendency to form water sprouts at scions.

*Bark.*—Immature: Smooth, green, RHS 141A. Mature: Yellow-green, RHS 147A.

*Leaf.*—Lanceolate, sharp pointed. Size: Small to medium, length: 74 mm; width 36 mm. Leaf blade: Firm, slightly concave in cross section, no undulation. Petioles: Wingless and short, 11 mm in length, 2 mm in diameter, Green RHS 146B. Color: Green RHS 147A (upper side); Yellow-green RHS 146B (lower side).

*Habit.*—Upright growing.

*Height.*—3–3.5 m.

*Disease resistance.*—No particular susceptibility or resistance observed.

*Trunk diameter.*—20 cm at 20 cm above the ground.

*Winter hardiness.*—Winter temperature in Bet Dagan, Israel averages 4–7 degrees Centigrade.

Flower:

*Flowering period.*—Late March, early April in Bet Dagan, Israel.

*Flower drop.*—April under growing conditions in Bet Dagan, Israel.

*Stamens.*—Approximately 20.

*Anther color.*—Pale yellow RHS 10C.

*Petal color.*—White RHS 155B.

*Petal number.*—5.

*Pollen fertility.*—Low, 6% stained with acetocarmine.

*Anthocyanin coloration.*—None.

Fruit:

*Shape.*—Oblate (52×110 mm).

*Size.*—Medium.

*Weight.*—115 g (based on average of 50 fruits).

*Color.*—Orange RHS 28B.

*Rind oil gland.*—Conspicuous.

*Number.*—Average (27/cm$^2$).

*Style.*—No persistence.

*Areola.*—Incompletely developed.

*Navel.*—Absent.

*Rind.*—Thin and easy to peel.

*Albedo.*—Yellow-orange RHS 19B.

*Flesh color.*—Orange RHS 25A.

*Fruit segments.*—9–11.

*Time to maturity.*—3–4 months (February–April in Israel).

*Fruit extract.*—(Test conducted Feb. 25, 1987). Total soluble solids (TSS). Acid content: 1.3%. TSS/acid ratio: 11.54. Flavor: Rich flavor.

Seeds:

*Size.*—10 mm length; 6 mm width.

*Color.*—External: White RHS 155C. Internal: Greyed crange RHS 165C.

*Cotyledons.*—Green white RHS 157D.

*Embrony.*—Polyembryony.

The tree and its fruit as described herein may vary in slight detail due to climate and/or soil conditions under which the variety is grown.

What is claimed is:

1. A new and distinct variety of *Citrus reticulata* tree substantially as herein described and shown.

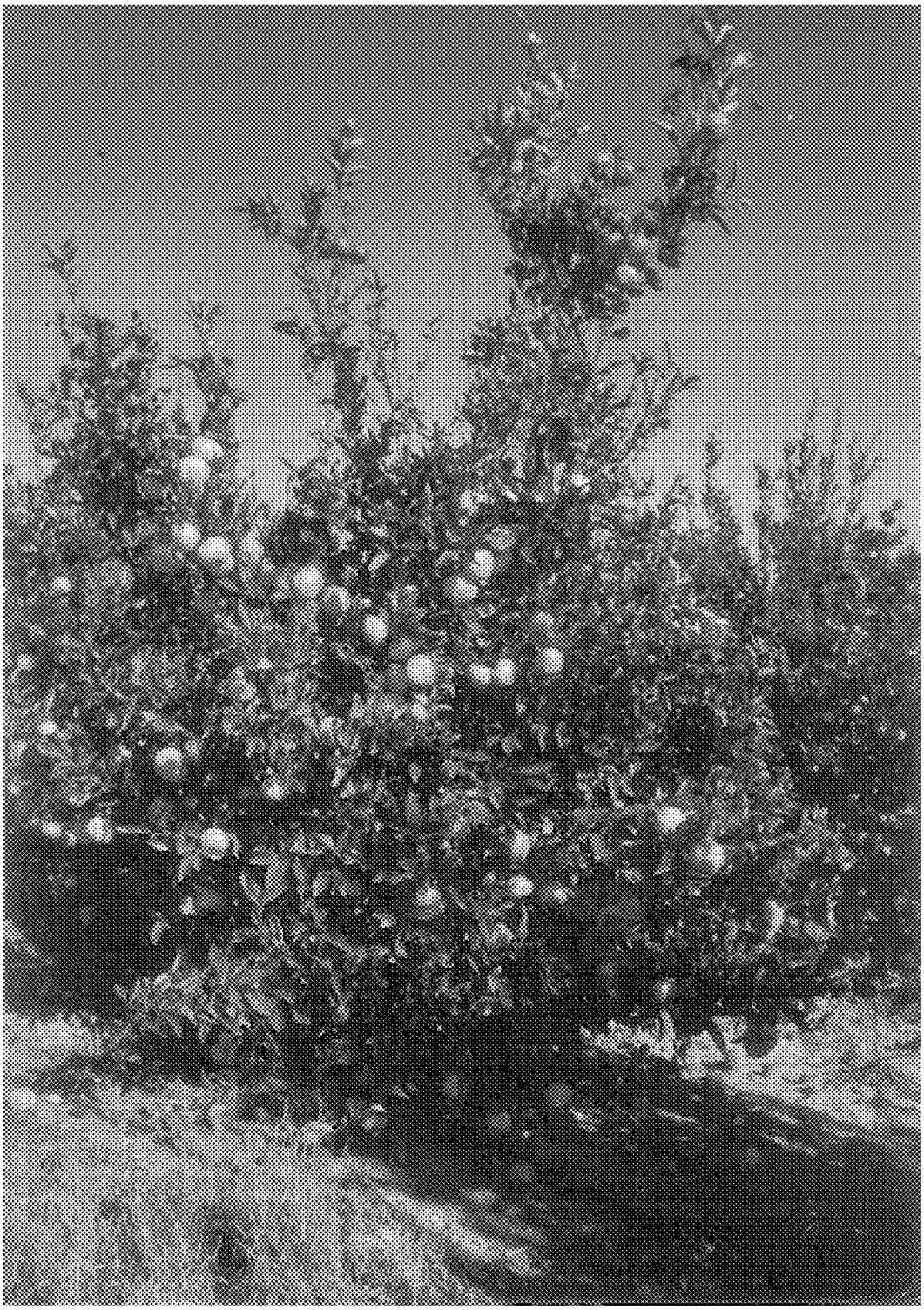

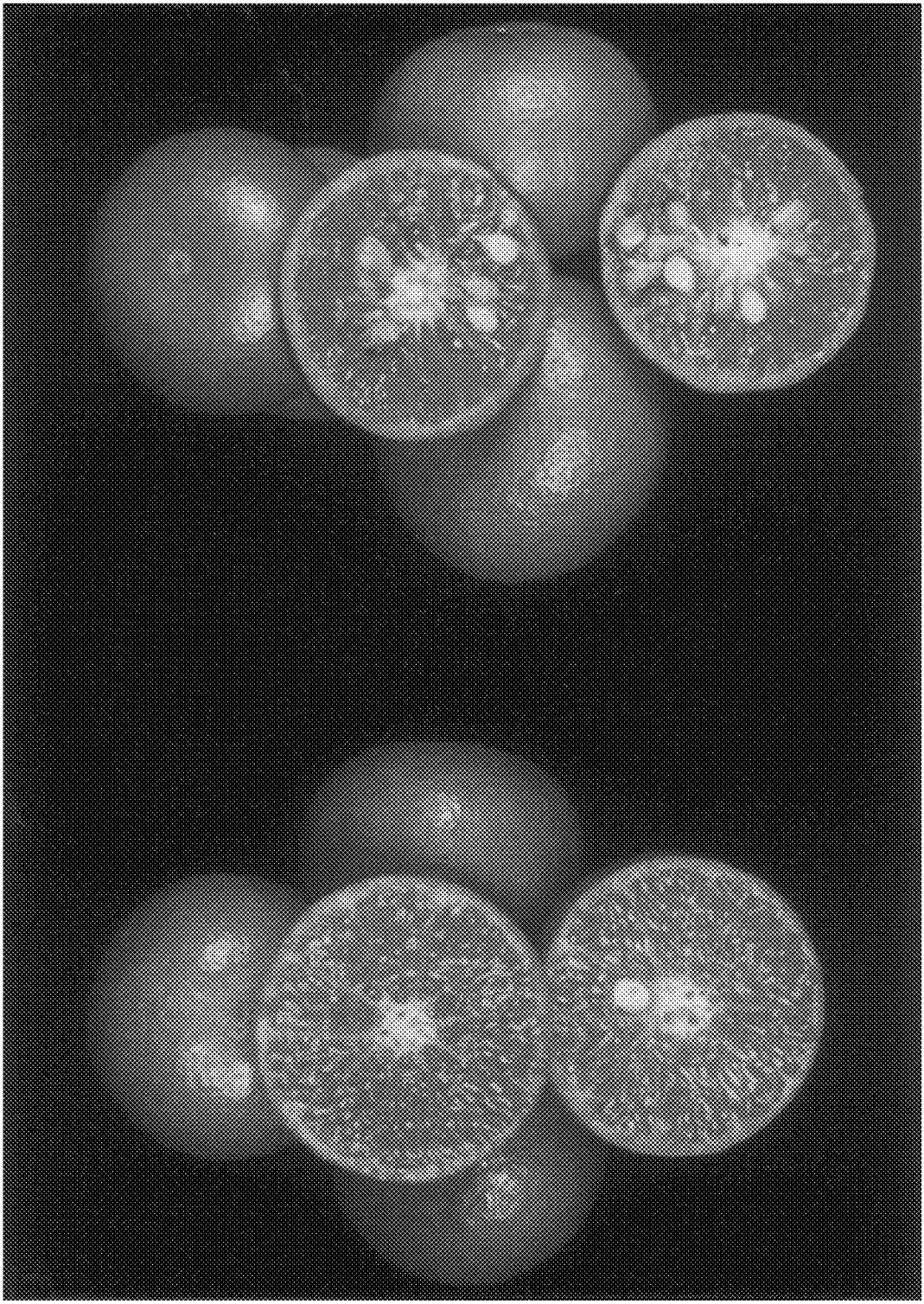

* * * * *